US007582479B2

(12) United States Patent
Thomson

(10) Patent No.: US 7,582,479 B2
(45) Date of Patent: *Sep. 1, 2009

(54) PRIMATE EMBRYONIC STEM CELL LINE

(75) Inventor: James A. Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

This patent is subject to a terminal disclaimer.

(21) Appl. No.: 11/036,245

(22) Filed: Jan. 14, 2005

(65) Prior Publication Data

US 2005/0164381 A1 Jul. 28, 2005

Related U.S. Application Data

(60) Continuation of application No. 09/982,637, filed on Oct. 18, 2001, now Pat. No. 7,029,913, which is a continuation of application No. 09/761,289, filed on Jan. 16, 2001, now abandoned, which is a continuation of application No. 09/106,390, filed on Jun. 26, 1998, now Pat. No. 6,200,806, which is a division of application No. 08/591,246, filed on Jan. 18, 1996, now Pat. No. 5,843,780, which is a continuation-in-part of application No. 08/376,327, filed on Jan. 20, 1995, now abandoned.

(51) Int. Cl.
*C12N 15/02* (2006.01)
*C12N 15/04* (2006.01)

(52) U.S. Cl. ...................... 435/366; 435/373

(58) Field of Classification Search .............. 435/366, 435/373, 377
See application file for complete search history.

(56) References Cited

U.S. PATENT DOCUMENTS

| | | | |
|---|---|---|---|
| 5,061,620 A | 10/1991 | Tsukamoto | |
| 5,166,065 A | 11/1992 | Williams et al. | |
| 5,340,740 A | 8/1994 | Petitte et al. | |
| 5,449,620 A | 9/1995 | Khillan | |
| 5,453,357 A | 9/1995 | Khillan et al. | |
| 5,523,226 A | 6/1996 | Wheeler | |
| 5,541,081 A | 7/1996 | Hardy | |
| 5,589,376 A | 12/1996 | Anderson et al. | |
| 5,591,625 A | 1/1997 | Gerson et al. | |
| 5,690,926 A * | 11/1997 | Hogan | 424/93.1 |
| 5,843,780 A | 12/1998 | Thomas | |
| 6,200,806 B1 | 3/2001 | Thomas | |
| 7,029,913 B2 * | 4/2006 | Thomson | 435/363 |
| 7,186,883 B2 | 3/2007 | Williams et al. | |

FOREIGN PATENT DOCUMENTS

WO   WO 94/03585   2/1994

OTHER PUBLICATIONS

Shamblott et al. (1998) PNAS, vol. 95, pp. 13726-13731.*

Shamblott et al. Derivation of Pluripotent Stem Cells from Cultured Human Primordial Germ Cells. Proced. Natl. Acad. Sci. (USA). Nov. 1998, vol. 95, pp. 13726-13731.*
Pera et al. Human Embryonic Stem Cells. J. Cell Science. 2000, vol. 113, pp. 5-10.*
Andrews, P., et al., Cell lines from human germ cell tumours, Teratocarcinoms and Embryonic Stem Cells; A Practical Approach, Oxford: 1RL Press, Ch. 8:207-248 (1987).
Andrews, P., et al., Pluripotent embryonal carcinoma clones derived from the human teratocarcinoma cell line Tera-2, Lab. Invest., 50(2):147-162 (1984).
Bongso, A., et al., Isolation and culture of inner cell mass cells from human blastocysts, Human Reprod., 9(1):2110-2117 (1994).
Bongso, A., et al., The growth of inner cell mass cells from human blastocysts, Theriogenology, 41:167 (1994).
Brown, D.G., et al., Criteria that optimize the potential of murine embryonic stem cells for in vitro and in vivo developmental studies, In Vitro Cell. Dev. Bio., 28(A)773-778 (1992).
Clark, A., et al., Germ line manipulation: applications in agriculture and biotechnology, Transgenic Animals, Grosveld et al. eds., 250 (1993).
Cruz, Y., et al., Origin of embryonic and extraembryonic cell lineages in mammalian embryos, Current Communications, 4:147-204 (1991).
Damjanov, I.., et al., Retinoic acid-induced differentiation of the developmentally pluripotent human germ cell tumor-derived cell line, NCCIT, Lab Invest., 68(2):220-232 (1993).
Doetschman, T., et al., Establishment of hamster blastocyst-derived embryonic etem (ES) cells, Developmental Biology, 127:224-227 (1988).
Doetschman, T., et al., The in vitro development of blastocyst-derived embryonic stem cell lines: formation of visceral yolk sac, blood islands and myocardium, J. Embrvol. Exp. Morph.. 87:27-45 (1985).
Evans, M., et al., Establishment in culture of pluripotential cells from mouse embryos, Nature, 292:154-156 (1981).
Evans, M., et al., Derivation and preliminary characterization of pluripotent cell lines from porcine and bovine blastocysts, Theriogenology, 33(1):125-128 (1990).
Giles, J., et al., Pluripotency of cultured rabbit inner cell mass cells detected by isozyme analysis and eye pigmentation of fetuses following injection into blastocysts or morulae, Mol. Reprod. Dev., 36:130-138 (1993).

(Continued)

*Primary Examiner*—Deborah Crouch
(74) *Attorney, Agent, or Firm*—Drinker Biddle & Reath, LLP

(57) ABSTRACT

A purified preparation of primate embryonic stem cells is disclosed. This preparation is characterized by the following cell surface markers: SSEA-1 (−); SSEA-4 (+); TRA-1-60 (+); TRA-1-81 (+); and alkaline phosphatase (+). In a particularly advantageous embodiment, the cells of the preparation are human embryonic stem cells, have normal karyotypes, and continue to proliferate in an undifferentiated state after continuous culture for eleven months. The embryonic stem cell lines also retain the ability, throughout the culture, to form trophoblast and to differentiate into all tissues derived from all three embryonic germ layers (endoderm, mesoderm and ectoderm). A method for isolating a primate embryonic stem cell line is also disclosed.

6 Claims, 8 Drawing Sheets

OTHER PUBLICATIONS

Golos, T., et al., Cloning of four growth hormone/chorionic somatomammotropin-related complementary deoxyribonucleic acids differentially expressed during pregnancy in the rhesus monkey placenta Endocrinology.

Graves, K., et al., Derivation and characterization of putative pluripotential embryonic stem cells from preimplantation rabbit embryos, Mol. Reprod. Dev., 36:424-433 (1993).

Labosky, P., et al., Mouse embryonic germ (EG) cell lines: transmission through the germline and differences in the methylation imprint of insulin-like growth factor 2 receptor (Igf2r) compared with embryonic stem (ES) cell lines, Development.

Lapidot, T., et al., Modeling human hematopoiesis in immunodeficient mice, Lab. Animal Sci., 43(2); 147-149 (1993).

Marshall, E., Rules on embryo research due out, Science, 265:1024-1026(1994).

Nichols, J., et al., Establishment of germ-line-competent embryonic stem (ES) cells using differentiation inhibiting activity, Development, 110:1341-1348 (1990).

Notarianni, E., et al., Maintenance and differentiation in culture of pluripotential embryonic cells lines from pig blastocysts, J. Reprod. Fert. Suppl., 41:51-56 (1990).

Notarianni, E., et al., Derivation of pluripotent,embryonic cell lines from the pig and sheep, J. Rep. & Fert. 43 255-260 (1991).

Piedrahita, J., Dissertation On Studies on the isolation of embryonic stem cells: Comparative behavior of murine, porcine and ovine embryos, University of California Davis 1989.

Piedrahita, et al., On the isolation of embryonic stem cells: Comparative behavior of murine, porcine and ovine embryos, Theriogenology, 34(5):879-901 (1990).

Rossantt, J., et al., The relationship between embryonic, embryonal carcinoma and embryo-derived stem cells, Cell Diff., 15:155-161 (1984).

Seshagiri, P., et al., Non-surgical uterine flushing for the recovery of preimplantation embryos in rhesus monkeys: lack of seasonal infertility, Am. J. Primatol., 29:81-91 (1993).

Strojek, R. et al., A method for cultivating morphologically undifferentiated embryonic stem cells from porcine blastocysts, Theriogenology 33 901-913 (1990).

Sukoyan, M., et al., Isolation and cultivation of blastocyst-derived stem cell lines from american mink (Mustela vision), Mol. Reprod. Dev., 33:418-431 (1992).

Sukoyan, M., et al., Embryonic stem cells derived from morulae, inner cell mass, and blastocysts of mink: comparisons of their pluripotencies, Mol. Reprod. Deve., 36:148-158 (1993).

Talbot, et al., Culturing The epiblast cells of the pig blastocyst, In Vitro Cell. Dev. Bio., 29(A):543-554 (1993).

Thomson, J., et al., Nonsurgical uterine stage preimplantation embryo collection from the common marmoset, J. Med. Primatol., 23:333-336 (1994).

Thomson, J., et al., Pluripotent cell lines derived from common marmoset (Callithrix jacchus) blastocysts, Biology of Reproduction, 55:254-259 (1996).

Ware, et al., Development of embryonic stem cell lines from farm animals, Biol. Reprod., 38(Suppl. 1):129 (1998).

Wenk, J., et al., Glycolipods of germ cell tumors: Extended globo-series glycolipods are a hallmark of human embryonal carcinoma cells, Int. J. Can, 58:108-115 (1994).

Williams, R., et al., Myeloid leukaemia inhibitory factor maintains the developmental potential of embryonic stem cells, Nature, 336:684-692 (1998).

Associated Press Milwaukee Journal Article, Embryonic Monkey Cells Isolated (Nov. 4, 1994).

Cherny, Ra, "Reproduction, Fertility and Development," CSIRO 6:569-575 (1994).

Reubinoff, et al. "Nature Biotech," 18:399-404 (2000).

Walsh, B., "Singapore," Time, Oct. 23, 2006.

Iannaccone et al., "Pluripotent Embryonic Stem Cells from the Rat Are Capable of Producing Chimeras," Dev Biol. 163: 288-292 (1994).

Martin, "Isolation of a pluripotent cell line from early mouse embryos cultured in medium conditioned by teratocarcinoma," PNAS 78:7634 (1981).

Ouhibi et al., "Initial Culture Behaviour of Rat Blastocysts on Selected Feeder Cell Lines," Mol. Reprod. & Dev. 40:311-324 (1995).

Sherman, "Long Term Culture of Cells Derived from Mouse Blastocysts," Differentiation, 11:51-67 (1975).

Stewart et al., "Blastocyst Implantation Depends on Maternal Expression of Leukaemia Inhibitory Factor," Nature 359:76-79 (1992).

Talbot et al., "In Vitro Pluripotency of Epiblasts Derived From Bovine Blastocysts," Mol. Reprod. & Dev. 42:35-52 (1995).

Thomson et al., "Isolation of a primate embryonic stem cell line," PNAS 92:7844-7848 (1995).

* cited by examiner

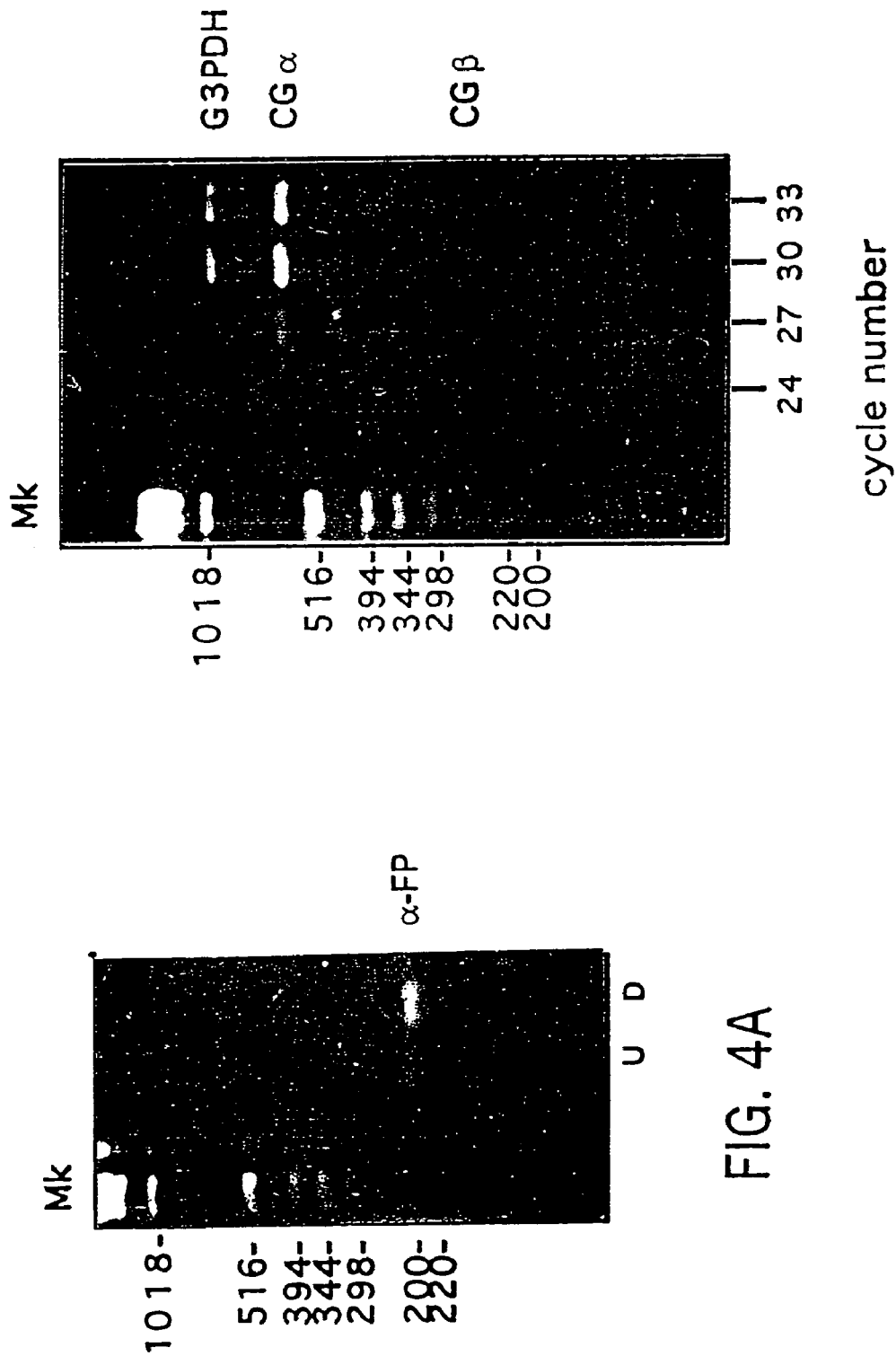

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 25 base pairs
      (B) TYPE: nucleic acid

```
            (C) STRANDEDNESS: double
            (D) TOPOLOGY: linear (ii) MOLECULE TYPE: DNA (genomic)

(xi) SEQUENCE DESCRIPTION: SEQ ID NO: 1:

GCTGGATTGT CTGCAGGATG GGGAA                                              25

(2) INFORMATION FOR SEQ ID NO: 2:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 2:

TCCCCTGAAG AAAATTGGTT AAAAT                                              25

(2) INFORMATION FOR SEQ ID NO: 3:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 3:

GGATCCACCG TCAACACCAC CATCTGTGC                                          29

(2) INFORMATION FOR SEQ ID NO: 4:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 4:

GGATCCACAG GTCAAAGGGT GGTCCTTGGG                                         30

(2) INFORMATION FOR SEQ ID NO: 5:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 5:

GGGAATTCGC AGTTACTGAG AACTCACAAG                                         30

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: double
            (D) TOPOLOGY: linear
```

```
    (ii) MOLECULE TYPE: DNA (genomic)

(xi) SEQUENCE DESCRIPTION: SEQ ID NO: 6:

GGGAATTCGA AGCATGTCAA AGTGGTATGG                                    30
```

PRIMATE EMBRYONIC STEM CELL LINE

CROSS-REFERENCE TO RELATED APPLICATIONS

This application is a continuation of U.S. Ser. No. 09/982,637, filed Oct. 18, 2001 now U.S. Pat. No. 7,029,913, which was a continuation of U.S. Ser. No. 09/761,289 filed Jan. 16, 2001, now abandoned, which was a continuation of U.S. Ser. No. 09/106,390 filed June 26, 1998, now U.S. Pat. No. 6,200,806, which was a continuation of U.S. Ser. No. 08/591,246 filed Jan. 18, 1996, now U.S. Pat. No. 5,843,780, which was a continuation-in-part of U.S. Ser. No. 08/376,327 filed Jan. 20, 1995, now abandoned.

STATEMENT REGARDING FEDERALLY SPONSORED RESEARCH OR DEVELOPMENT

This invention was made with United States government support awarded by NIH NCRR Grant No. RR00167. The United States government has certain rights in this invention.

BACKGROUND OF THE INVENTION

In general, the field of the present invention is stem cell cultures. Specifically, the field of the present invention is primate embryonic stem cell cultures.

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

One of the seminal achievements of mammalian embryology of the last decade is the routine insertion of specific genes into the mouse genome through the use of mouse ES cells. This alteration has created a bridge between the in vitro manipulations of molecular biology and an understanding of gene function in the intact animal. Mouse ES cells are undifferentiated, pluripotent cells derived in vitro from preimplantation embryos (Evans, et al. *Nature* 292: 154-159, 1981; Martin, *Proc. Natl. Acad. Sci. USA* 78: 7634-7638, 1981) or from fetal germ cells (Matsui, et al., *Cell* 70: 841-847, 1992). Mouse ES cells maintain an undifferentiated state through serial passages when cultured in the presence of fibroblast feeder layers in the presence of Leukemia Inhibitory Factor (LIF) (Williams, et al., *Nature* 336: 684-687, 1988). If LIF is removed, mouse ES cells differentiate.

Mouse ES cells cultured in non-attaching conditions aggregate and differentiate into simple embryoid bodies, with an outer layer of endoderm and an inner core of primitive ectoderm. If these embryoid bodies are then allowed to attach onto a tissue culture surface, disorganized differentiation occurs of various cell types, including nerves, blood cells, muscle, and cartilage (Martin, 1981, supra; Doetschman, et al., *J. Embryol. Exp. Morph.* 87: 27-45, 1985). Mouse ES cells injected into syngeneic mice form teratocarcinomas that exhibit disorganized differentiation, often with representatives of all three embryonic germ layers. Mouse ES cells combined into chimeras with normal preimplantation embryos and returned to the uterus participate in normal development (Richard, et al., *Cytogenet. Cell Genet.* 65: 169-171, 1994).

The ability of mouse ES cells to contribute to functional germ cells in chimeras provides a method for introducing site-specific mutations into mouse lines. With appropriate transfection and selection strategies, homologous recombination can be used to derive ES cell lines with planned alterations of specific genes. These genetically altered cells can be used to form chimeras with normal embryos and chimeric animals are recovered. If the ES cells contribute to the germ line in the chimeric animal, then in the next generation a mouse line for the planned mutation is established.

Because mouse ES cells have the potential to differentiate into any cell type in the body, mouse ES cells allow the in vitro study of the mechanisms controlling the differentiation of specific cells or tissues. Although the study of mouse ES cells provides clues to understanding the differentiation of general mammalian tissues, dramatic differences in primate and mouse development of specific lineages limits the usefulness of mouse ES cells as a model of human development. Mouse and primate embryos differ meaningfully in the timing of expression of the embryonic genome, in the formation of an egg cylinder versus an embryonic disc (Kaufman, *The Atlas of Mouse Development*, London: Academic Press, 1992), in the proposed derivation of some early lineages (O'Rahilly & Muller, *Developmental Stages in Human Embryos*, Washington: Carnegie Institution of Washington, 1987), and in the structure and function in the extraembryonic membranes and placenta (Mossman, *Vertebrate Fetal Membranes*, New Brunswick: Rutgers, 1987). Other tissues differ in growth factor requirements for development (e.g. the hematopoietic system (Lapidot et al., *Lab An Sci* 43: 147-149, 1994)), and in adult structure and function (e.g. the central nervous system). Because humans are primates, and development is remarkably similar among primates, primate ES cells lines will provide a faithful model for understanding the differentiation of primate tissues in general and human tissues in particular.

The placenta provides just one example of how primate ES cells will provide an accurate model of human development that cannot be provided by ES cells from other species. The placenta and extraembryonic membranes differ dramatically between mice and humans. Structurally, the mouse placenta is classified as labyrinthine, whereas the human and the rhesus monkey placenta are classified as villous. Chorionic gonadotropin, expressed by the trophoblast, is an essential molecule involved in maternal recognition of pregnancy in all primates, including humans (Heam, *J Reprod Fertil* 76: 809-819, 1986; Heam et al., *J Reprod Fert* 92: 497-509, 1991). Trophoblast secretion of chorionic gonadotropin in primates maintains the corpus luteum of pregnancy and, thus, progesterone secretion. Without progesterone, pregnancy fails. Yet mouse trophoblast produces no chorionic gonadotropin, and mice use entirely different mechanisms for pregnancy maintenance (Heam et al., "Normal and abnormal embryo-fetal development in mammals," In: Lamming E, ed. *Marshall's Physiology of Reproduction*. 4th ed. Edinburgh, N.Y.: Churchill Livingstone, 535-676, 1994). An immortal, euploid, primate ES cell line with the developmental potential to form trophoblast in vitro, will allow the study of the ontogeny and function of genes such as chorionic gonadotropin which are critically important in human pregnancy. Indeed, the differentiation of any tissue for which there are significant differences between mice and primates will be more accurately reflected in vitro by primate ES cells than by mouse ES cells.

The major in vitro models for studying trophoblast function include human choriocarcinoma cells, which are malignant cells that may not faithfully reflect normal trophectoderm; short-term primary cultures of human and non-human primate cytotrophoblast, which in present culture conditions quickly form non-dividing syncytial trophoblast; and in vitro culture of preimplantation non-human primate embryos (Hearn, et al., *J. Endocrinol.* 119: 249-255, 1988; Coutifaris, et al., *Ann. NY Acad. Sci.* 191-201, 1994). An immortal, euploid, non-human primate embryonic stem (ES) cell line with the developmental potential to form trophectoderm offers significant advantages over present in vitro models of human trophectoderm development and function, as trophoblast-specific genes such as chorionic gonadotropin could be stably altered in the ES cells and then studied during differentiation to trophectoderm.

The cell lines currently available that resembles primate ES cells most closely are human embryonic carcinoma (EC) cells, which are pluripotent, immortal cells derived from teratocarcinomas (Andrews, et al., *Lab. Invest.* 50 (2): 147-162, 1984; Andrews, et al., in: Robertson E., ed. *Teratocarcinomas and Embryonic Stem Cells: A Practical Approach*. Oxford: IRL press, pp. 207-246, 1987). EC cells can be induced to differentiate in culture, and the differentiation is characterized by the loss of specific cell surface markers (SSEA-3, SSEA-4, TRA-1-60, and TRA-1-81) and the appearance of new markers (Andrews, et al., 1987, supra). Human EC cells will form teratocarcinomas with derivatives of multiple embryonic lineages in tumors in nude mice. However, the range of differentiation of these human EC cells is limited compared to the range of differentiation obtained with mouse ES cells, and all EC cell lines derived to date are aneuploid (Andrews, et al., 1987, supra). Similar mouse EC cell lines have been derived from teratocarcinomas, and, in general their developmental potential is much more limited than mouse ES cells (Rossant, et al., *Cell Differ.* 15: 155-161, 1984). Teratocarcinomas are tumors derived from germ cells, and although germ cells (like ES cells) are theoretically totipotent (i.e. capable of forming all cell types in the body), the more limited developmental potential and the abnormal karyotypes of EC cells are thought to result from selective pressures in the teratocarcinoma tumor environment (Rossant & Papaioannou, *Cell Differ* 15: 155-161, 1984). ES cells, on the other hand, are thought to retain greater developmental potential because they are derived from normal embryonic cells in vitro, without the selective pressures of the teratocarcinoma environment. Nonetheless, mouse EC cells and mouse ES cells share the same unique combination of cell surface markers (SSEA-1 (+), SSEA-3 (−), SSEA-4 (−), and alkaline phosphatase (+)).

Pluripotent cell lines have also been derived from preimplantation embryos of several domestic and laboratory animals species (Evans, et al., *Theriogenology* 33 (1): 125-128, 1990; Evans, et al., *Theriogenology* 33 (1): 125-128, 1990; Notarianni, et al., *J. Reprod. Fertil.* 41 (Suppl.): 51-56, 1990; Giles, et al., *Mol. Reprod. Dev.* 36: 130-138, 1993; Graves, et al., *Mol. Reprod. Dev.* 36: 424-433, 1993; Sukoyan, et al., *Mol. Reprod. Dev.* 33: 418-431, 1992; Sukoyan, et al., *Mol. Reprod. Dev.* 36: 148-158, 1993; Iannaccone, et al., *Dev. Biol.* 163: 288-292, 1994).

Whether or not these cell lines are true ES cells lines is a subject about which there may be some difference of opinion. True ES cells should: (i) be capable of indefinite proliferation in vitro in an undifferentiated state; (ii) maintain a normal karyotype through prolonged culture; and (iii) maintain the potential to differentiate to derivatives of all three embryonic germ layers (endoderm, mesoderm, and ectoderm) even after prolonged culture. Strong evidence of these required properties have been published only for rodents ES cells including mouse (Evans & Kaufman, *Nature* 292: 154-156, 1981; Martin, *Proc Natl Acad Sci USA* 78: 7634-7638, 1981) hamster (Doetschman et al. *Dev Biol* 127: 224-227, 1988), and rat (Iannaccone et al. *Dev Biol* 163: 288-292, 1994), and less conclusively for rabbit ES cells (Giles et al. *Mol Reprod Dev* 36: 130-138, 1993; Graves & Moreadith, *Mol Reprod Dev* 36: 424-433, 1993). However, only established ES cell lines from the rat (Iannaccone, et al., 1994, supra) and the mouse (Bradley, et al, *Nature* 309: 255-256, 1984) have been reported to participate in normal development in chimeras. There are no reports of the derivation of any primate ES cell line.

BRIEF SUMMARY OF THE INVENTION

The present invention is a purified preparation of primate embryonic stem cells. The primate ES cell lines are true ES cell lines in that they: (i) are capable of indefinite proliferation in vitro in an undifferentiated state; (ii) are capable of differentiation to derivatives of all three embryonic germ layers (endoderm, mesoderm, and ectoderm) even after prolonged culture; and (iii) maintain a normal karyotype throughout prolonged culture. The true primate ES cells lines are therefore pluripotent.

The present invention is also summarized in that primate ES cell lines are preferably negative for the SSEA-1 marker, preferably positive for the SSEA-3 marker, and positive for the SSEA-4 marker. The primate ES cell lines are also positive for the TRA-1-60, and TRA-1-81 markers, as well as positive for the alkaline phosphatase marker.

It is an advantageous feature of the present invention that the primate ES cell lines continue to proliferate in an undifferentiated state after continuous culture for at least one year. In a particularly advantageous embodiment, the cells remain euploid after proliferation in an undifferentiated state.

It is a feature of the primate ES cell lines in accordance with the present invention that the cells can differentiate to trophoblast in vitro and express chorionic gonadotropin.

The present invention is also a purified preparation of primate embryonic stem cells that has the ability to differentiate into cells derived from mesoderm, endoderm, and ectoderm germ layers after the cells have been injected into an immunocompromised mouse, such as a SCID mouse.

The present invention is also a method of isolating a primate embryonic stem cell line. The method comprises the steps of isolating a primate blastocyst, isolating cells from the inner cellular mass (ICM) of the blastocyst, plating the ICM cells on a fibroblast layer (wherein ICM-derived cell masses are formed) removing an ICM-derived cell mass and dissociating the mass into dissociated cells, replating the dissociated cells on embryonic feeder cells and selecting colonies with compact morphology containing cells with a high nucleus/cytoplasm ratio, and prominent nucleoli. The cells of the selected colonies are then cultured.

It is an object of the present invention to provide a primate embryonic stem cell line.

It is an object of the present invention to provide a primate embryonic stem cell line characterized by the following markers: alkaline phosphatase(+); SSEA-1(−); preferably SSEA-3(+); SSEA-4(+); TRA-1-60(+); and TRA-1-81(+).

It is an object of the present invention to provide a primate embryonic stem cell line capable of proliferation in an undifferentiated state after continuous culture for at least one year. Preferably, these cells remain euploid.

It is another object of the present invention to provide a primate embryonic stem cell line wherein the cells differentiate into cells derived from mesoderm, endoderm, and ectoderm germ layers when the cells are injected into an immunocompromised mouse.

Other objects, features, and advantages of the present invention will become obvious after study of the specification, drawings, and claims.

BRIEF DESCRIPTION OF THE SEVERAL VIEWS OF THE DRAWINGS

FIGS. 4A-4B are photographs illustrating expression of α-fetoprotein mRNA and α- and β-chorionic gonadotrophin mRNA expression in rhesus ES cells (R278.5) allowed to differentiate in culture.

Figure 1:
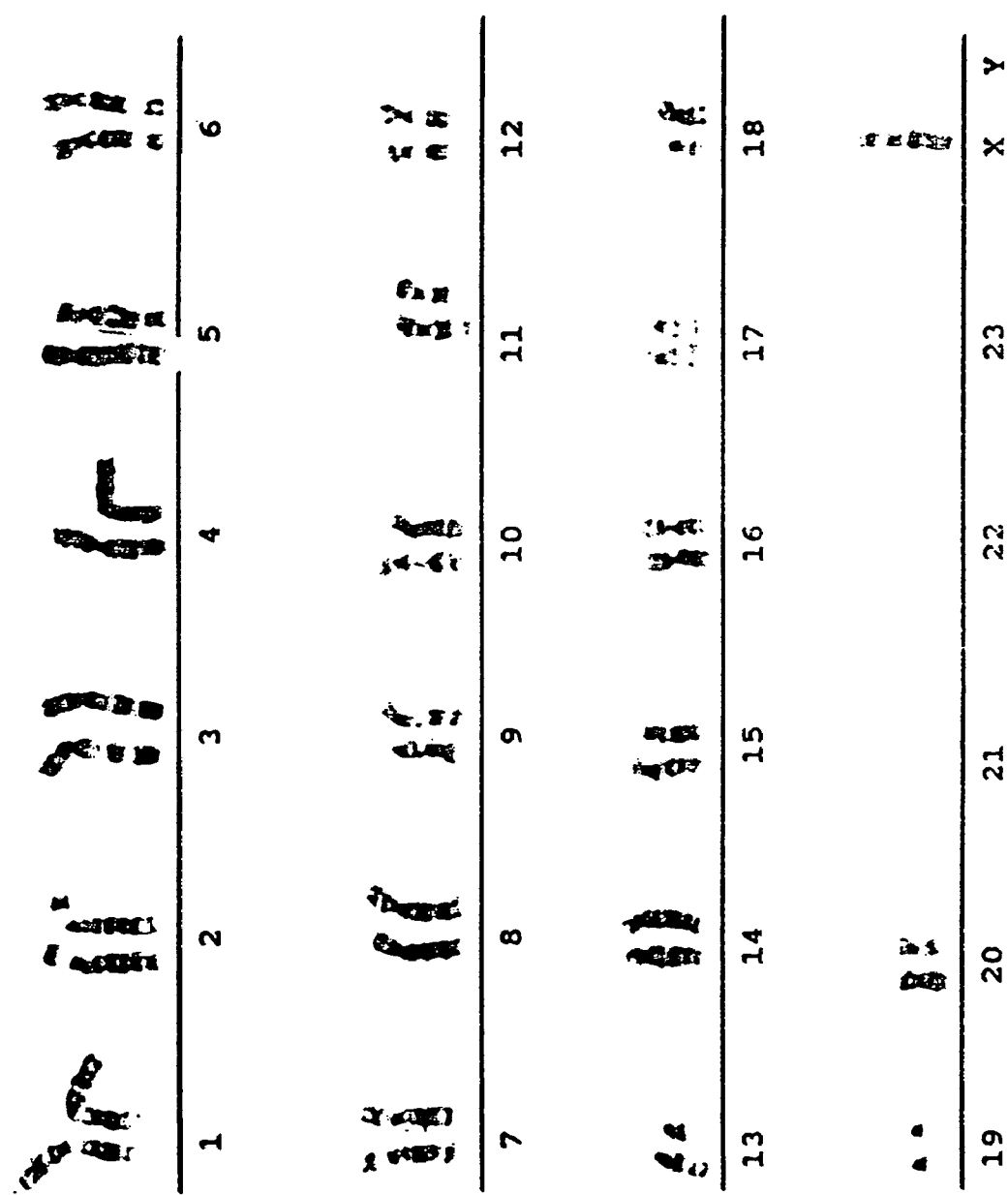
FIG. 1 is a photomicrograph illustrating normal XY karyotype of rhesus ES cell line R278.5 after 11 months of continuous culture.

DETAILED DESCRIPTION OF THE INVENTION (1) In General (a) Uses of Primate ES Cells The present invention is a pluripotent, immortal euploid primate ES cell line, as exemplified by the isolation of ES cell lines from two primate species, the common marmoset (*Callithrix jacchus*) and the rhesus monkey (*Macaca mulatta*). Primate embryonic stem cells are useful for:

(i) Generating transgenic non-human primates for models of specific human genetic diseases. Primate embryonic stem cells will allow the generation of primate tissue or animal models for any human genetic disease for which the responsible gene has been cloned. The human genome project will identify an increasing number of genes related to human disease, but will not always provide insights into gene function. Transgenic nonhuman primates will be essential for elucidating mechanisms of disease and for testing new therapies.

(ii) Tissue transplantation. By manipulating culture conditions, primate ES cells, human and non-human, can be induced to differentiate to specific cell types, such as blood cells, neuron cells, or muscle cells. Alternatively, primate ES cells can be allowed to differentiate in tumors in SCID mice, the tumors can be disassociated, and the specific differentiated cell types of interest can be selected by the usage of lineage specific markers through the use of fluorescent activated cell sorting (FACS) or other sorting method or by direct microdissection of tissues of interest. These differentiated cells could then be transplanted back to the adult animal to treat specific diseases, such as hematopoietic disorders, endocrine deficiencies, degenerative neurological disorders or hair loss.

(b) Selection of Model Species

Macaques and marmosets were used as exemplary species for isolation of a primate ES cell line. Macaques, such as the rhesus monkey, are Old World species that are the major primates used in biomedical research. They are relatively large (about 7-10 kg). Males take 4-5 years to mature, and females have single young. Because of the extremely close anatomical and physiological similarities between humans and rhesus monkeys, rhesus monkey true ES cell lines provide a very accurate in vitro model for human differentiation. Rhesus monkey ES cell lines and rhesus monkeys will be particularly useful in the testing of the safety and efficacy of the transplantation of differentiated cell types into whole animals for the treatment of specific diseases or conditions. In addition, the techniques developed for the rhesus ES cell lines model the generation, characterization and manipulation of human ES cell lines.

The common marmoset (*Callithrix jacchus*) is a New World primate species with reproductive characteristics that make it an excellent choice for ES cell derivation. Marmosets are small (about 350-400 g), have a short gestation period (144 days), reach sexual maturity in about 18 months, and routinely have twins or triplets. Unlike in macaques, it is possible to routinely synchronize ovarian cycles in the marmoset with prostaglandin analogs, making collection of age-matched embryos from multiple females possible, and allowing efficient embryo transfer to synchronized recipients with 70%-80% of embryos transferred resulting in pregnancies. Because of these reproductive characteristics that allow for the routine efficient transfer of multiple embryos, marmosets provide an excellent primate species in which to generate transgenic models for human diseases.

There are approximately 200 primate species in the world. The most fundamental division that divides higher primates is between Old World and New world species. The evolutionary distance between the rhesus monkey and the common marmoset is far greater than the evolutionary distance between humans and rhesus monkeys. Because it is here demonstrated that it is possible to isolate ES cell lines from a representative species of both the Old World and New World group using similar conditions, the techniques described below may be used successfully in deriving ES cell lines in other higher primates as well. Given the close evolutionary distance between rhesus macaques and humans, and the fact that feeder-dependent human EC cell lines can be grown in conditions similar to those that support primate ES cell lines, the same growth conditions will allow the isolation and growth of human ES cells. In addition, human ES cell lines will be permanent cell lines that will also be distinguished from all other permanent human cell lines by their normal karyotype and the expression of the same combination of cell surface markers (alkaline phosphotase, preferably SSEA-3, SSEA-4, TRA-1-60 and TRA-1-81) that characterize other primate ES cell lines. A normal karyotype and the expression of this combination of cell surface markers will be defining properties of true human ES cell lines, regardless of the method used for their isolation and regardless of their tissue of origin.

No other primate (human or non-human) ES cell line is known to exist. The only published permanent, euploid, embryo-derived cell lines that have been convincingly demonstrated to differentiate into derivatives of all three germ layers have been derived from rodents (the mouse, rat, and hamster), and possibly from rabbit. The published reports of embryo-derived cell lines from domestic species have failed to convincingly demonstrate differentiation of derivatives of all three embryonic germ layers or have not been permanent cell lines. Research groups in Britain and Singapore are informally reported, later than the work described here, to have attempted to derive human ES cell lines from surplus in vitro fertilization-produced human embryos, although they have not yet reported success in demonstrating pluripotency of their cells and have failed to isolate permanent cell lines. In the only published report on attempts to isolate human ES cells, conditions were used (LIF in the absence of fibroblast feeder layers) that the results below will indicate will not result in primate ES cells which can remain in an undifferentiated state. It is not surprising, then that the cells grown out of human ICMs failed to continue to proliferate after 1 or 2 subcultures, Bongso et al. *Hum. Reprod.* 9: 2100-2117 (1994).

(2) Embryonic Stem Cell Isolation

A preferable medium for isolation of embryonic stem cells is "ES medium." ES medium consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Preferably, fetal bovine serum batches are compared by testing clonal plating efficiency of a low passage mouse ES cell line ($ES_{jt3}$), a cell line developed just for the purpose of this test. FBS batches must be compared because it has been found that batches vary dramatically in their ability to support embryonic cell growth, but any other method of assaying the competence of FBS batches for support of embryonic cells will work as an alternative.

Primate ES cells are isolated on a confluent layer of murine embryonic fibroblast in the presence of ES cell medium. Embryonic fibroblasts are preferably obtained from 12 day old fetuses from outbred CF1 mice (SASCO), but other strains may be used as an alternative. Tissue culture dishes are preferably treated with 0.1% gelatin (type I; Sigma).

For rhesus monkey embryos, adult female rhesus monkeys (greater than four years old) demonstrating normal ovarian cycles are observed daily for evidence of menstrual bleeding (day 1 of cycle=the day of onset of menses). Blood samples are drawn daily during the follicular phase starting from day 8 of the menstrual cycle, and serum concentrations of luteinizing hormone are determined by radioimmunoassay. The female is paired with a male rhesus monkey of proven fertility from day 9 of the menstrual cycle until 48 hours after the luteinizing hormone surge; ovulation is taken as the day following the luteinizing hormone surge. Expanded blastocysts are collected by non-surgical uterine flushing at six days after ovulation. This procedure routinely results in the recovery of an average 0.4 to 0.6 viable embryos per rhesus monkey per month, Seshagiri et al. *Am J Primatol* 29: 81-91, 1993.

For marmoset embryos, adult female marmosets (greater than two years of age) demonstrating regular ovarian cycles are maintained in family groups, with a fertile male and up to five progeny. Ovarian cycles are controlled by intramuscular injection of 0.75 g of the prostaglandin PGF2a analog cloprostenol (Estrumate, Mobay Corp, Shawnee, Kans.) during the middle to late luteal phase. Blood samples are drawn on day 0 (immediately before cloprostenol injection), and on days 3, 7, 9, 11, and 13. Plasma progesterone concentrations are determined by ELISA. The day of ovulation is taken as the day preceding a plasma progesterone concentration of 10 ng/ml or more. At eight days after ovulation, expanded blastocysts are recovered by a non-surgical uterine flush procedure, Thomson et al. "Non-surgical uterine stage preimplantation embryo collection from the common marmoset," *J Med Primatol,* 23: 333-336 (1994). This procedure results in the average production of 1.0 viable embryos per marmoset per month.

The zona pellucida is removed from blastocysts by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes.

After two further washes in DMEM, lysed trophectoderm cells are removed from the intact inner cell mass (ICM) by gentle pipetting, and the ICM plated on mouse inactivated (3000 rads gamma irradiation) embryonic fibroblasts.

After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are replated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (without calcium or magnesium and with 2 mM EDTA) every 1-2 weeks as the cultures become dense. Early passage cells are also frozen and stored in liquid nitrogen.

Cell lines may be karyotyped with a standard G-banding technique (such as by the Cytogenetics Laboratory of the University of Wisconsin State Hygiene Laboratory, which provides routine karyotyping services) and compared to published karyotypes for the primate species.

Isolation of ES cell lines from other primate species would follow a similar procedure, except that the rate of development to blastocyst can vary by a few days between species, and the rate of development of the cultured ICMs will vary between species. For example, six days after ovulation, rhesus monkey embryos are at the expanded blastocyst stage, whereas marmoset embryos don't reach the same stage until 7-8 days after ovulation. The Rhesus ES cell lines were obtained by splitting the ICM-derived cells for the first time at 7-16 days after immunosurgery; whereas the marmoset ES cells were derived with the initial split at 7-10 days after immunosurgery. Because other primates also vary in their developmental rate, the timing of embryo collection, and the timing of the initial ICM split will vary between primate species, but the same techniques and culture conditions will allow ES cell isolation.

Because ethical considerations in the U.S. do not allow the recovery of human in vivo fertilized preimplantation embryos from the uterus, human ES cells that are derived from preimplantation embryos will be derived from in vitro fertilized (IVF) embryos. Experiments on unused (spare) human IVF-produced embryos are allowed in many countries, such as Singapore and the United Kingdom, if the embryos are less than 14 days old. Only high quality embryos are suitable for ES isolation. Present defined culture conditions for culturing the one cell human embryo to the expanded blastocyst are suboptimal but practicable, Bongso et al., *Hum Reprod* 4: 706-713, 1989. Co-culturing of human embryos with human oviductal cells results in the production of high blastocyst quality. IVF-derived expanded human blastocysts grown in cellular co-culture, or in improved defined medium, will allow the isolation of human ES cells with the same procedures described above for nonhuman primates.

(3) Defining Characteristics of Primate ES Cells

Primate embryonic stem cells share features with the primate ICM and with pluripotent human embryonal carcinoma cells. Putative primate ES cells may therefore be characterized by morphology and by the expression of cell surface markers characteristic of human EC cells. Additionally, putative primate ES cells may be characterized by developmental potential, karyotype and immortality.

(a) Morphology

The colony morphology of primate embryonic stem cell lines is similar to, but distinct from, mouse embryonic stem cells. Both mouse and primate ES cells have the characteristic features of undifferentiated stem cells, with high nuclear/cytoplasmic ratios, prominent nucleoli, and compact colony formation. The colonies of primate ES cells are flatter than mouse ES cell colonies and individual primate ES cells can be easily distinguished. In FIG. 2, reference character A indicates a phase contrast photomicrograph of cell line R278.5 demonstrating the characteristic primate ES cell morphology.

(b) Cell Surface Markers

A primate ES cell line of the present invention is distinct from mouse ES cell lines by the presence or absence of the cell surface markers described below.

One set of glycolipid cell surface markers is known as the Stage-specific embryonic antigens 1 through 4. These antigens can be identified using antibodies for SSEA 1, preferably SSEA-3 and SSEA-4 which are available from the Developmental Studies Hybridoma Bank of the National Institute of Child Health and Human Development. The cell surface markers referred to as TRA-1-60 and TRA-1-81 designate antibodies from hybridomas developed by Peter Andrews of the University of Sheffield and are described in Andrews et al., "Cell lines from human germ cell tumors," In: Robertson E, ed. *Teratocarcinomas and Embryonic Stem Cells: A Practical Approach.* Oxford: IRL Press, 207-246, 1987. The antibodies were localized with a biotinylated secondary antibody and then an avidin/biotinylated horseradish peroxidase complex (Vectastain ABC System, Vector Laboratories). Alternatively, it should also be understood that other antibodies for these same cell surface markers can be generated. NTERA-2 cl. D1, a pluripotent human EC cell line (gift of Peter Andrews), may be used as a negative control for SSEA-1, and as a positive control for SSEA-3, SSEA-4, TRA-1-60, and TRA-1-81. This cell line was chosen for positive control only because it has been extensively studied and reported in the literature, but other human EC cell lines may be used as well.

Mouse ES cells ($ES_{jt3}$) are used as a positive control for SSEA-1, and for a negative control for SSEA-3, SSEA-4, TRA-1-60, and TRA-1-81. Other routine negative controls include omission of the primary or secondary antibody and substitution of a primary antibody with an unrelated specificity.

Alkaline phosphatase may be detected following fixation of cells with 4% para-formaldehyde using "Vector Red" (Vector Laboratories) as a substrate, as described by the manufacturer (Vector Laboratories). The precipitate formed by this substrate is red when viewed with a rhodamine filter system, providing substantial amplification over light microscopy.

Table 1 diagrams a comparison of mouse ES cells, primate ES cells, and human EC cells. The only cells reported to express the combination of markers SSEA-3, SSEA-4, TRA-1-60, and TRA-1-81 other than primate ES cells are human EC cells. The globo-series glycolipids SSEA-3 and SSEA-4 are consistently present on human EC cells, and are of diagnostic value in distinguishing human EC cell tumors from human yolk sac carcinomas, choriocarcinomas, and other lineages which lack these markers, Wenk et al., *Int J Cancer* 58:108-115, 1994. A recent survey found SSEA-3 and SSEA-4 to be present on all of over 40 human EC cell lines examined, Wenk et al. TRA-1-60 and TRA-1-81 antigens have been studied extensively on a particular pluripotent human EC cell line, NTERA-2 CL. D1, Andrews et al, supra. Differentiation of NTERA-2 CL. D1 cells in vitro results in the loss of SSEA-3, SSEA-4, TRA-1-60, and TRA-1-81 expression and the increased expression of the lacto-series glycolipid SSEA-1, Andrews et al, supra. This contrasts with undifferentiated mouse ES cells, which express SSEA-1, and neither SSEA-3 nor SSEA-4. Although the function of these antigens are unknown, their shared expression by R278.5 cells and human EC cells suggests a close embryological similarity. Alkaline phosphatase will also be present on all primate ES cells. A successful primate ES cell culture of the present invention will correlate with the cell surface markers found in the rhesus macaque and marmoset cell lines described in Table 1.

As disclosed below in Table 1, the rhesus macaque and marmoset cell lines are identical to human EC cell lines for the 5 described markers. Therefore, a successful primate ES cell culture will also mimic human EC cells. However, there are other ways to discriminate ES cells from EC cells. For example, the primate ES cell line has a normal karyotype and the human EC cell line is aneuploid.

In FIG. 3, the photographs labelled A through F demonstrate the characteristic staining of these markers on a rhesus monkey ES cell line designated R278.5.

TABLE 1

|  | Mouse ES | C. jacchus ES | M. mulatta ES | Human EC (NTERA-2 cl.D1) |
| --- | --- | --- | --- | --- |
| SSEA-1 | + | − | − | − |
| SSEA-3 | − | + | + | + |
| SSEA-4 | − | + | + | + |

TABLE 1-continued

|  | Mouse ES | C. jacchus ES | M. mulatta ES | Human EC (NTERA-2 cl.D1) |
|---|---|---|---|---|
| Tra-1-60 | − | + | + | + |
| Tra-1-81 | − | + | + | + |

(c) Developmental Potential

Primate ES cells of the present invention are pluripotent. By "pluripotent" we mean that the cell has the ability to develop into any cell derived from the three main germ cell layers or an embryo itself. When injected into SCID mice, a successful primate ES cell line will differentiate into cells derived from all three embryonic germ layers including: bone, cartilage, smooth muscle, striated muscle, and hematopoietic cells (mesoderm); liver, primitive gut and respiratory epithelium (endoderm); neurons, glial cells, hair follicles, and tooth buds (ectoderm).

This experiment can be accomplished by injecting approximately $0.5$-$1.0 \times 10^6$ primate ES cells into the rear leg muscles of 8-12 week old male SCID mice. The resulting tumors can be fixed in 4% paraformaldehyde and examined histologically after paraffin embedding at 8-16 weeks of development. In FIG. 4, photomicrographs designated A-F are of sections of tumors formed by injection of rhesus ES cells into the hind leg muscles of SCID mice and analyzed 15 weeks later demonstrating cartilage, smooth muscle, and striated muscle (mesoderm); stratified squamous epithelium with hair follicles, neural tube with ventricular, intermediate, and mantle layers (ectoderm); ciliated columnar epithelium and villi lined by absorptive enterocytes and mucus-secreting goblet cells (endoderm).

A successful nonhuman primate ES cell line will have the ability to participate in normal development when combined in chimeras with normal preimplantation embryos. Chimeras between preimplantation nonhuman primate embryos and nonhuman primate ES cells can be formed by routine methods in several ways. (i) injection chimeras: 10-15 nonhuman primate ES cells can be microinjected into the cavity of an expanded nonhuman primate blastocyst; (ii) aggregation chimeras: nonhuman primate morulae can be co-cultured on a lawn of nonhuman primate ES cells and allowed to aggregate; and (iii) tetraploid chimeras: 10-15 nonhuman primate ES cells can be aggregated with tetraploid nonhuman primate morulae obtained by electrofusion of 2-cell embryos, or incubation of morulae in the cytoskeletal inhibitor cholchicine. The chimeras can be returned to the uterus of a female nonhuman primate and allowed to develop to term, and the ES cells will contribute to normal differentiated tissues derived from all three embryonic germ layers and to germ cells. Because nonhuman primate ES can be genetically manipulated prior to chimera formation by standard techniques, chimera formation followed by embryo transfer can lead to the production of transgenic nonhuman primates.

(d) Karyotype

Successful primate ES cell lines have normal karyotypes. Both XX and XY cells lines will be derived. The normal karyotypes in primate ES cell lines will be in contrast to the abnormal karyotype found in human embryonal carcinoma (EC), which are derived from spontaneously arising human germ cell tumors (teratocarcinomas). Human embryonal carcinoma cells have a limited ability to differentiate into multiple cell types and represent the closest existing cell lines to primate ES cells. Although tumor-derived human embryonal carcinoma cell lines have some properties in common with embryonic stem cell lines, all human embryonal carcinoma cell lines derived to date are aneuploid. Thus, primate ES cell lines and human EC cell lines can be distinguished by the normal karyotypes found in primate ES cell lines and the abnormal karyotypes found in human EC lines. By "normal karyotype" it is meant that all chromosomes normally characteristic of the species are present and have not been noticeably altered.

Because of the abnormal karyotypes of human embryonal carcinoma cells, it is not clear how accurately their differentiation reflects normal differentiation. The range of embryonic and extra-embryonic differentiation observed with primate ES cells will typically exceed that observed in any human embryonal carcinoma cell line, and the normal karyotypes of the primate ES cells suggests that this differentiation accurately recapitulates normal differentiation.

(e) Immortality

Immortal cells are capable of continuous indefinite replication in vitro. Continued proliferation for longer than one year of culture is a sufficient evidence for immortality, as primary cell cultures without this property fail to continuously divide for this length of time (Freshney, *Culture of animal cells*. New York: Wiley-Liss, 1994). Primate ES cells will continue to proliferate in vitro with the culture conditions described above for longer than one year, and will maintain the developmental potential to contribute all three embryonic germ layers. This developmental potential can be demonstrated by the injection of ES cells that have been cultured for a prolonged period (over a year) into SCID mice and then histologically examining the resulting tumors. Although karyotypic changes can occur randomly with prolonged culture, some primate ES cells will maintain a normal karyotype for longer than a year of continuous culture.

(f) Culture Conditions

Growth factor requirements to prevent differentiation are different for the primate ES cell line of the present invention than the requirements for mouse ES cell lines. In the absence of fibroblast feeder layers, Leukemia inhibitory factor (LIF) is necessary and sufficient to prevent differentiation of mouse ES cells and to allow their continuous passage. Large concentrations of cloned LIF fail to prevent differentiation of primate ES cell lines in the absence of fibroblast feeder layers. In this regard, primate ES stem cells are again more similar to human EC cells than to mouse ES cells, as the growth of feeder-dependent human EC cells lines is not supported by LIF in the absence of fibroblasts.

(g) Differentiation to Extra Embryonic Tissues

When grown on embryonic fibroblasts and allowed to grow for two weeks after achieving confluence (i.e., continuously covering the culture surface), primate ES cells of the present invention spontaneously differentiate and will produce chorionic gonadotropin, indicating trophoblast differentiation (a component of the placenta) and produce α-fetoprotein, indicating endoderm differentiation. Chorionic gonadotropin activity can be assayed in the medium conditioned by differentiated cells by Leydig cell bioassay, Seshagiri & Hearn, *Hum Reprod* 8: 279-287, 1992. For mRNA analysis, RNA can be prepared by guanidine isothiocyanate-phenol/chloroform extraction (1) from approximately $0.2 \times 10^6$ differentiated cells and from $0.2 \times 10^6$ undifferentiated cells. The relative levels of the mRNA for α-fetoprotein and the α- and β-subunit of chorionic gonadotropin relative to glyceraldehyde-3-phosphate dehydrogenase can be determined by semi-quantitative Reverse Transcriptase-Polymerase Chain Reaction (RT-PCR). The PCR primers for glyceraldehyde 3-phosphate dehydrogenase (G3PDH), obtained from Clontech (Palo Alto, Calif.), are based on the human cDNA sequence, and do not amplify mouse G3PDH mRNA under our conditions. Primers for the α-fetoprotein mRNA are based on the human sequence and flank the 7th intron (5' primer=(5') GCTGGAT-TGTCTGCAGGATGGGGAA (SEQ ID NO: 1); 3' primer= (5') TCCCCTGAAGAAAATTGGTTAAAAT (SEQ ID NO: 2)). They amplify a cDNA of 216 nucleotides. Primers for the β-subunit of chorionic gonadotropin flank the second intron (5' primer=(5') ggatc CACCGTCAACACCACCATCT-GTGC (SEQ ID NO: 3); 3' primer=(5') ggatc CACAGGT-CAAAGGGTGGTCCTTGGG (SEQ ID NO: 4)) (nucleotides added to the hCGb sequence to facilitate sub-cloning are shown in lower case italics). They amplify a cDNA of 262 base pairs. The primers for the CGα subunit can be based on sequences of the first and fourth exon of the rhesus gene (5' primer=(5') gggaattc GCAGTTACTGAGAACTCACAAG (SEQ ID NO: 5); 3' primer=(5') gggaattc GAAGCATGT-CAAAGTGGTATGG (SEQ ID NO: 6)) and amplify a cDNA of 556 base pairs. The identity of the α-fetoprotein, CGα and CGβ cDNAs can be verified by subcloning and sequencing.

For Reverse Transcriptase-Polymerase Chain Reaction (RT-PCR), 1 to 5 µl of total R278.5 RNA can be reverse transcribed as described Golos et al. *Endocrinology* 133 (4): 1744-1752, 1993, and one to 20 µl of reverse transcription reaction was then subjected to the polymerase chain reaction in a mixture containing 1-12.5 pmol of each G3PDH primer, 10-25 pmol of each mRNA specific primer, 0.25 mM dNTPs (Pharmacia, Piscataway, N.J.), 1×AmpliTaq buffer (final reaction concentrations=10 mM Tris, pH 8.3, 50 mM KCl, 1.5 mM MgCl2, 0.001% (w/v) gelatin) 2.5 µCi of deoxycytidine 5'a[$^{32}$P]triphosphate (DuPont, Boston, Mass.), 10% glycerol and 1.25 U of AmpliTaq (Perkin-Elmer, Oak Brook, Ill.) in a total volume of 50 µl. The number of amplification rounds which produced linear increases in target cDNAs and the relation between input RNA and amount of PCR product is empirically determined as by Golos et al. Samples were fractionated in 3% Nusieve (FMC, Rockland, Me.) agarose gels (1×TBE running buffer) and DNA bands of interest were cut out, melted at 65° C. in 0.5 ml TE, and radioactivity determined by liquid scintillation counting. The ratio of counts per minute in a specific PCR product relative to cpm of G3PDH PCR product is used to estimate the relative levels of a mRNAs among differentiated and undifferentiated cells.

The ability to differentiate into trophectoderm in vitro and the ability of these differentiated cells to produce chorionic gonadotropin distinguishes the primate ES cell line of the present invention from all other published ES cell lines.

EXAMPLES (1) Animals and Embryos

As described above, we have developed a technique for non-surgical, uterine-stage embryo recovery from the rhesus macaque and the common marmoset.

To supply rhesus embryos to interested investigators, The Wisconsin Regional Primate Research Center (WRPRC) provides a preimplantation embryo recovery service for the rhesus monkey, using the non-surgical flush procedure described above. During 1994, 151 uterine flushes were attempted from rhesus monkeys, yielding 80 viable embryos (0.53 embryos per flush attempt).

By synchronizing the reproductive cycles of several marmosets, significant numbers of in vivo produced, age-matched, preimplantation primate embryos were studied in controlled experiments for the first time. Using marmosets from the self-sustaining colony (250 animals) of the Wisconsin Regional Primate Research Center (WRPRC), we recovered 54 viable morulae or blastocysts, 7 unfertilized oocytes or degenerate embryos, and 5 empty zonae pellucidae in a total of 54 flush attempts (1.0 viable embryo-flush attempt). Marmosets have a 28 day ovarian cycle, and because this is a non-surgical procedure, females can be flushed on consecutive months, dramatically increasing the embryo yield compared to surgical techniques which require months of rest between collections.

(2) Rhesus Macaque Embryonic Stem Cells

Using the techniques described above, we have derived three independent embryonic stem cell lines from two rhesus monkey blastocysts (R278.5, R366, and R367). One of these, R278.5, remains undifferentiated and continues to proliferate after continuous culture for over one year. R278.5 cells have also been frozen and successfully thawed with the recovery of viable cells.

Figure 2A:
FIGS. 2A-2D are a set of phase-contrast photomicrographs demonstrating the morphology of undifferentiated rhesus ES (R278.5) cells and of cells differentiated from R278.5 in vitro (bar=100μ). Photograph 2A demonstrates the distinct cell borders, high nucleus to cytoplasm ratio, and prominent nucleoli of undifferentiated rhesus ES cells. Photographs 2B-2D shows differentiated cells eight days after plating R278.5 cells on gel treated tissue culture plastic (with $10^3$ units/ml added human LIF). Cells of these three distinct morphologies are consistently present when R278.5 cells are allowed to differentiate at low density without fibroblasts either in the presence or absence of soluble human LIF.
Figure 2B:
Figure 2C:
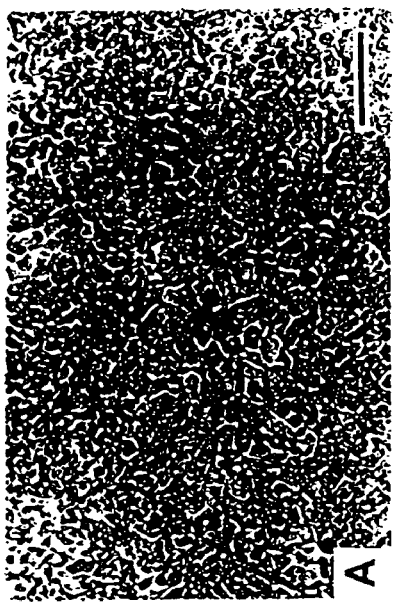
Figure 2D:
Figure 3A:
FIGS. 3A-F are photomicrographs demonstrating the expression of cell surface markers on undifferentiated rhesus ES (R278.5) cells (bar=100μ). Photograph 3A shows Alkaline Phosphatase (+); Photograph 3B shows SSEA-1 (−); Photograph 3C shows SSEA-3 (+); Photograph 3D shows SSEA-4 (+); Photograph 3E shows TRA-1-60 (+); and Photograph 3F shows TRA-1-81 (+).
Figure 3B:
Figure 3C:
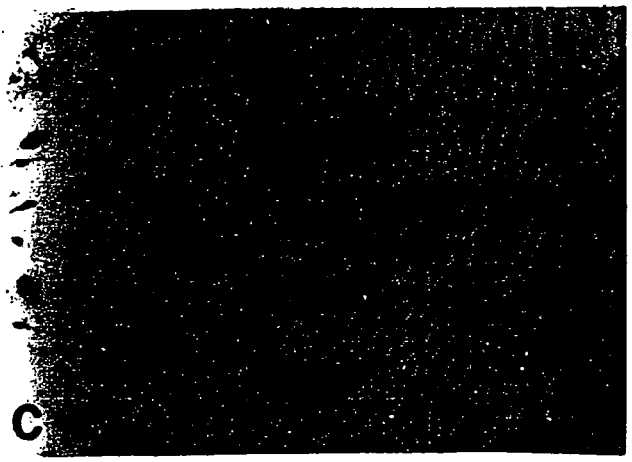
Figure 3D:
Figure 3E:
Figure 3F:
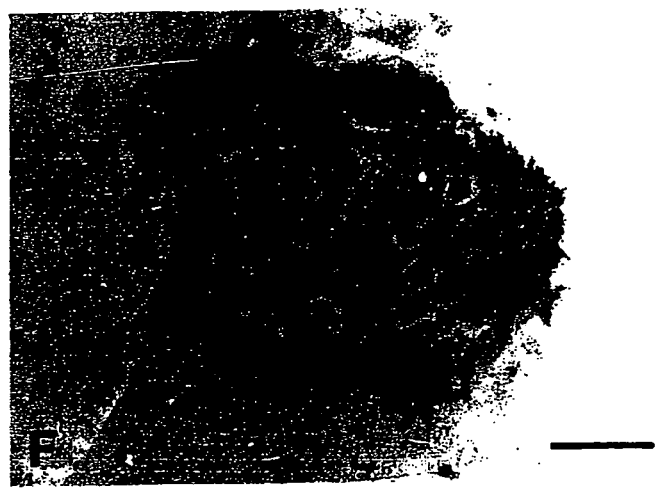
Figure 5A:
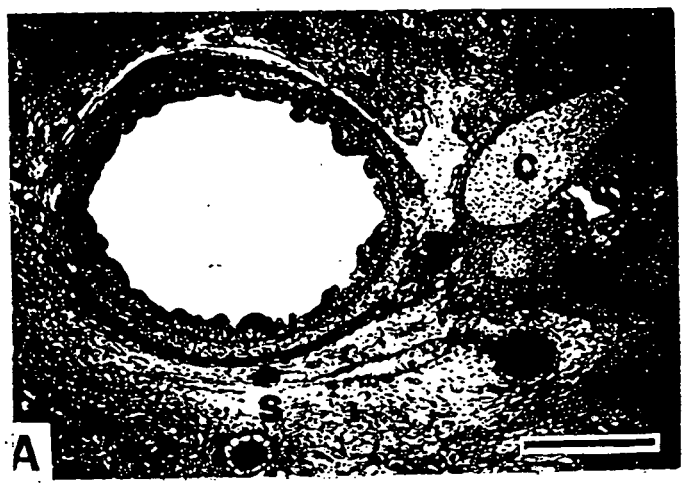
FIGS. 5A-5F include six photomicrographs of sections of tumors formed by injection of $0.5 \times 10^6$ rhesus ES (R278.5) cells into the hindleg muscles of SCID mice and analyzed 15 weeks later. Photograph 5A shows a low power field demonstrating disorganized differentiation of multiple cell types. A gut-like structure is encircled by smooth muscle(s), and elsewhere foci of cartilage (c) are present (bar=400μ); Photograph 5B shows striated muscle (bar=40μ); Photograph 5C shows stratified squamous epithelium with several hair follicles. The labeled hair follicle (f) has a visible hair shaft (bar=200μ); Photograph 5D shows stratified layers of neural cells in the pattern of a developing neural tube. An upper "ventricular" layer, containing numerous mitotic figures (arrows), overlies a lower "mantle" layer. (bar=100μ); Photograph 5E shows ciliated columnar epithelium (bar=40μ); Photograph 5F shows villi covered with columnar epithelium with interspersed mucus-secreting goblet cells (bar=200μ).
Figure 5B:
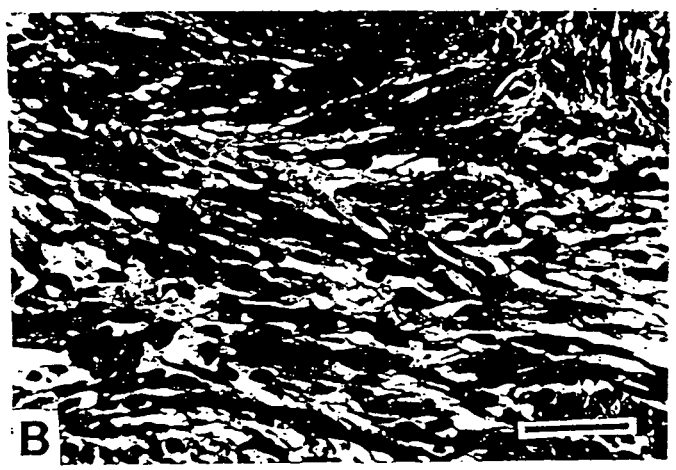
Figure 5C:
Figure 5D:
Figure 5E:
Figure 5F:

The morphology and cell surface markers of R278.5 cells are indistinguishable from human EC cells, and differ significantly from mouse ES cells. R278.5 cells have a high nucleus/cytoplasm ratio and prominent nucleoli, but rather than forming compact, piled-up colonies with indistinct cell borders similar to mouse ES cells, R278.5 cells form flatter colonies with individual, distinct cells (FIG. 2A). R278.5 cells express the SSEA-3, SSEA-4, TRA-1-60, and TRA-81 antigens (FIG. 3 and Table 1), none of which are expressed by mouse ES cells. The only cells known to express the combination of markers SSEA-3, SSEA-4, TRA-1-60, and TRA-1-81 other than primate ES cells are human EC cells. The globo-series glycolipids SSEA-3 and SSEA-4 are consistently present on human EC cells, and are of diagnostic value in distinguishing human EC cell tumors from yolk sac carcinomas, choriocarcinomas and other stem cells derived from human germ cell tumors which lack these markers, Wenk et al, *Int J Cancer* 58: 108-115, 1994. A recent survey found SSEA-3 and SSEA-4 to be present on all of over 40 human EC cell lines examined (Wenk et al.).

TRA-1-60 and TRA-1-81 antigens have been studied extensively on a particular pluripotent human EC cell line, NTERA-2 CL. D1 (Andrews et al.). Differentiation of NTERA-2 CL. D1 cells in vitro results in the loss of SSEA-3, SSEA-4, TRA-1-60, and TRA-1-81 expression and the increased expression of the lacto-series glycolipid SSEA-1. Undifferentiated mouse ES cells, on the other hand, express SSEA-1, and not SSEA-3, SSEA-4, TRA-1-60 or TRA-1-81 (Wenk et al.). Although the function of these antigens is unknown, their expression by R278.5 cells suggests a close embryological similarity between primate ES cells and human EC cells, and fundamental differences between primate ES cells and mouse ES cells.

R278.5 cells also express alkaline phosphatase. The expression of alkaline phosphatase is shared by both primate and mouse ES cells, and relatively few embryonic cells express this enzyme. Positive cells include the ICM and primitive ectoderm (which are the most similar embryonic cells in the intact embryo to ES cells), germ cells, (which are totipotent), and a very limited number of neural precursors, Kaufman M H. *The atlas of mouse development*. London: Academic Press, 1992. Cells not expressing this enzyme will not be primate ES cells.

Although cloned human LIF was present in the medium at cell line derivation and for initial passages, R278.5 cells grown on mouse embryonic fibroblasts without exogenous LIF remain undifferentiated and continued to proliferate. R278.5 cells plated on gelatin-treated tissue culture plates without fibroblasts differentiated to multiple cell types or failed to attach and died, regardless of the presence or absence of exogenously added human LIF (FIG. 2). Up to $10^4$ units/ml human LIF fails to prevent differentiation. In addition, added LIF fails to increase the cloning efficiency or proliferation rate of R278.5 cells on fibroblasts. Since the derivation of the R278.5 cell line, we have derived two additional rhesus ES cell lines (R366 and R367) on embryonic fibroblasts without any exogenously added LIF at initial derivation. R366 and R367 cells, like R278.5 cells, continue to proliferate on embryonic fibroblasts without exogenously added LIF and differentiate in the absence of fibroblasts, regardless of the presence of added LIF. RT-PCR performed on mRNA from spontaneously differentiated R278.5 cells revealed α-fetoprotein mRNA (FIG. 4). α-fetoprotein is a specific marker for endoderm, and is expressed by both extra-embryonic (yolk sac) and embryonic (fetal liver and intestines) endoderm-derived tissues. Epithelial cells resembling extraembryonic endoderm are present in cells differentiated in vitro from R278.5 cells (FIG. 2). Bioactive CG (3.89 ml units/ml) was present in culture medium collected from differentiated cells, but not in medium collected from undifferentiated cells (less than 0.03 ml units/ml), indicating the differentiation of trophoblast, a trophectoderm derivative. The relative level of the CGα mRNA increased 23.9-fold after differentiation (FIG. 4).

All SCID mice injected with R278.5 cells in either intra-muscular or intra-testicular sites formed tumors, and tumors in both sites demonstrated a similar range of differentiation. The oldest tumors examined (15 weeks) had the most advanced differentiation, and all had abundant, unambiguous derivatives of all three embryonic germ layers, including gut and respiratory epithelium (endoderm); bone, cartilage, smooth muscle, striated muscle (mesoderm); ganglia, glia, neural precursors, and stratified squamous epithelium (ectoderm), and other unidentified cell types (FIG. 5). In addition to individual cell types, there was organized development of some structures which require complex interactions between different cell types. Such structures included gut lined by villi with both absorptive enterocytes and mucus-secreting goblet cells, and sometimes encircled by layers of smooth muscle in the same orientation as muscularis mucosae (circular) and muscularis (outer longitudinal layer and inner circular layer); neural tubes with ventricular, intermediate, and mantle layers; and hair follicles with hair shafts (FIG. 5).

The essential characteristics that define R278.5 cells as ES cells include: indefinite (greater than one year) undifferentiated proliferation in vitro, normal karyotype, and potential to differentiate to derivatives of trophectoderm and all three embryonic germ layers. In the mouse embryo, the last cells capable of contributing to derivatives of both trophectoderm and ICM are early ICM cells. The timing of commitment to ICM or trophectoderm has not been established for any primate species, but the potential of rhesus ES cells to contribute to derivatives of both suggests that they most closely resemble early totipotent embryonic cells. The ability of rhesus ES cells to form trophoblast in vitro distinguishes primate ES cell lines from mouse ES cells. Mouse ES cell have not been demonstrated to form trophoblast in vitro, and mouse trophoblast does not produce gonadotropin. Rhesus ES cells and mouse ES cells do demonstrate the similar wide range of differentiation in tumors that distinguishes ES cells from EC cells. The development of structures composed of multiple cell types such as hair follicles, which require inductive interactions between the embryonic epidermis and underlying mesenchyme, demonstrates the ability of rhesus ES cells to participate in complex developmental processes.

The rhesus ES lines R366 and R367 have also been further cultured and analyzed. Both lines have a normal XY karyotype and were proliferated in an undifferentiated state for about three months prior to freezing for later analysis. Samples of each of the cell lines R366 and R367 were injected into SCID mice which then formed teratomas identical to those formed by R278.5 cells. An additional rhesus cell line R394 having a normal XX karyotype was also recovered. All three of these cell lines, R366, R367 and R394 are identical in morphology, growth characteristics, culture requirements and in vitro differentiation characteristics, i.e. the trait of differentiation to multiple cell types in the absence of fibroblasts, to cell line 278.5.

It has been determined that LIF is not required either to derive or proliferate these ES cultures. Each of the cell lines R366, R367 and R394 were derived and cultured without exogenous LIF.

It has also been demonstrated that the particular source of fibroblasts for co-culture is not critical. Several fibroblast cell lines have been tested both with rhesus line R278.5 and with the marmoset cell lines described below. The fibroblasts tested include mouse STO cells (ATCC 56-X), mouse 3T3 cells (ATCC 48-X), primary rhesus monkey embryonic fibroblasts derived from 36 day rhesus fetuses, and mouse Sl/Sl$^4$ cells, which are deficient in the steel factor. All these fibroblast cell lines were capable of maintaining the stem cell lines in an undifferentiated state. Most rapid proliferation of the stem cells was observed using primary mouse embryonic fibroblasts.

Unlike mouse ES cells, neither rhesus ES cells nor feeder-dependent human EC cells remain undifferentiated and proliferate in the presence of soluble human LIF without fibroblasts. The factors that fibroblasts produce that prevent the differentiation of rhesus ES cells or feeder-dependent human EC cells are unknown, but the lack of a dependence on LIF is another characteristic that distinguishes primate ES cells from mouse ES cells. The growth of rhesus monkey ES cells in culture conditions similar to those required by feeder-dependent human EC cells, and the identical morphology and cell surface markers of rhesus ES cells and human EC cells, suggests that similar culture conditions will support human ES cells.

Rhesus ES cells will be important for elucidating the mechanisms that control the differentiation of specific primate cell types. Given the close evolutionary distance and the developmental and physiological similarities between humans and rhesus monkeys, the mechanisms controlling the differentiation of rhesus cells will be very similar to the mechanisms controlling the differentiation of human cells. The importance of elucidating these mechanisms is that once they are understood, it will be possible to direct primate ES cells to differentiate to specific cell types in vitro, and these specific cell types can be used for transplantation to treat specific diseases.

Because ES cells have the developmental potential to give rise to any differentiated cell type, any disease that results in part or in whole from the failure (either genetic or acquired) of specific cell types will be potentially treatable through the transplantation of cells derived from ES cells. Rhesus ES cells and rhesus monkeys will be invaluable for testing the efficacy and safety of the transplantation of specific cell types derived from ES cells. A few examples of human diseases potentially treatable by this approach with human ES cells include degenerative neurological disorders such as Parkinson's disease (dopanergic neurons), juvenile onset diabetes (pancreatic β-islet cells) or Acquired Immunodeficiency Disease (lymphocytes). Because undifferentiated ES cells can proliferate indefinitely in vitro, they can be genetically manipulated with standard techniques either to prevent immune rejection after transplantation, or to give them new genetic properties to combat specific diseases. For specific cell types where immune rejection can be prevented, cells derived from rhesus monkey ES cells or other non-human primate ES cells could be used for transplantation to humans to treat specific diseases.

(3) Marmoset Embryonic Stem Cells

Our method for creating an embryonic stem cell line is described above. Using isolated ICM's derived by immunosurgery from marmoset blastocysts, we have isolated 7 putative ES cell lines, each of which have been cultured for over 6 months.

One of these, Cj11, was cultured continuously for over 14 months, and then frozen for later analysis. The Cj11 cell line and other marmoset ES cell lines have been successfully frozen and then thawed with the recovery of viable cells. These cells have a high nuclear/cytoplasmic ratio, prominent nucleoli, and a compact colony morphology similar to the pluripotent human embryonal carcinoma (EC) cell line NT2/D2.

Four of the cell lines we have isolated have normal XX karyotypes, and one has a normal XY karyotype (Karyotypes were performed by Dr. Charles Harris, University of Wisconsin). These cells were positive for a series of cell surface markers (alkaline phosphatase, SSEA-3, SSEA-4, TRA-1-60, and TRA-1-81) that in combination are definitive markers for undifferentiated human embryonal carcinoma cells (EC) cells and primate ES cells. In particular, these markers distinguish EC cells from the earliest lineages to differentiate in the human preimplantation embryo, trophectoderm (represented by BeWO choriocarcinoma cells) and extraembryonic endoderm (represented by 1411H yolk sac carcinoma cells).

When the putative marmoset ES cells were removed from fibroblast feeders, they differentiated into cells of several distinct morphologies. Among the differentiated cells, trophectoderm is indicated by the secretion of chorionic gonadotropin and the presence of the chorionic gonadotropin β-subunit mRNA. 12.7 mIU/ml luteinizing hormone (LH) activity was measured in the WRPRC core assay lab using a mouse Leydig cell bioassay in medium conditioned 24 hours by putative ES cells allowed to differentiate for one week. Note that chorionic gonadotrophin has both LH and FSH activity, and is routinely measured by LH assays. Control medium from undifferentiated ES cells had less than 1 mIU/ml LH activity.

Chorionic gonadotropin β-subunit mRNA was detected by reverse transcriptase-polymerase chain reaction (RT-PCR). DNA sequencing confirmed the identity of the chorionic gonadotrophin β-subunit.

Endoderm differentiation (probably extraembryonic endoderm) was indicated by the presence of α-fetoprotein mRNA, detected by RT-PCR.

Figure 6A:
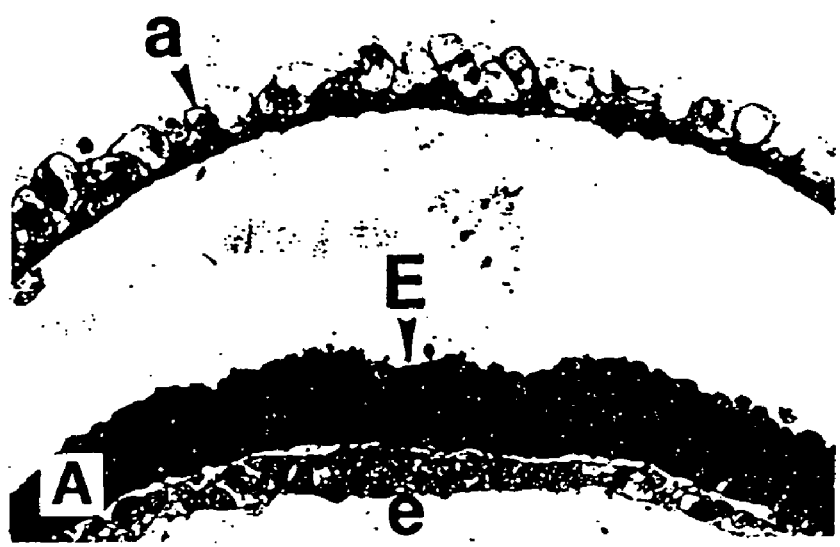
FIGS. 6A-6B include photographs of an embryoid Body. This embryoid body was formed from a marmoset ES cell line (Cj62) that had been continuously passaged in vitro for over 6 months. Photograph 6A (above) shows a section of the anterior ⅓ of the embryonic disc. Note the primitive ectoderm (E) forms a distinct cell layer from the underlying primitive endoderm (e), with no mixing of the cell layers. Note also that amnion (a) is composed of two distinct layers; the inner layer is continuous with the primitive ectoderm at the margins. Photograph 6B (below) shows a section in the caudal ⅓ of embryonic disc. Note central groove (arrow) and mixing of primitive ectoderm and endoderm representing early primitive streak formation, indicating the beginning of gastrulation. 400×, toluidine blue stain.
Figure 6B:
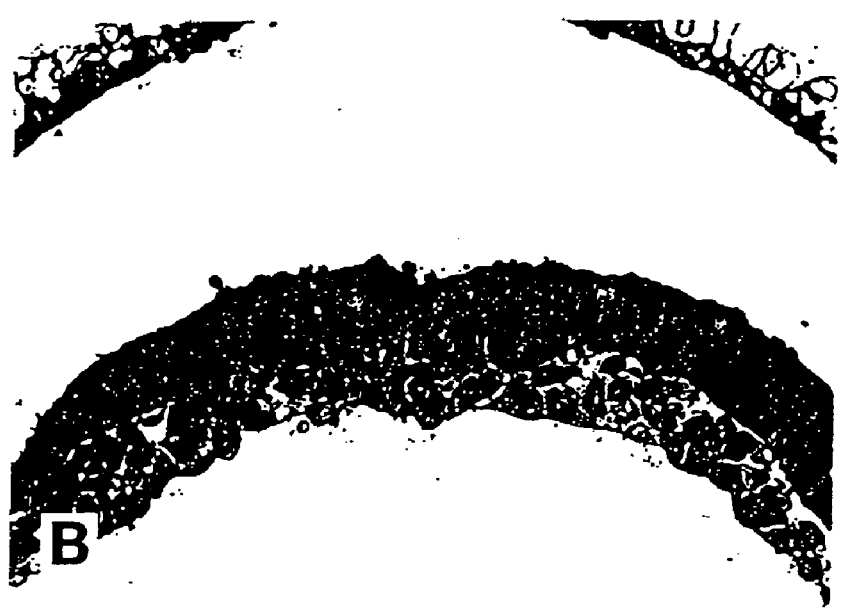

When the marmoset ES cells were grown in high densities, over a period of weeks epithelial cells differentiated and covered the culture dish. The remaining groups of undifferentiated cells rounded up into compact balls and then formed embryoid bodies (as shown in FIG. 6) that recapitulated early development with remarkable fidelity. Over 3-4 weeks, some of the embryoid bodies formed a bilaterally symmetric pyriform embryonic disc, an amnion, a yolk sac, and a mesoblast outgrowth attaching the caudal pole of the amnion to the culture dish.

Histological and ultrastructural examination of one of these embryoid bodies (formed from a cell line that had been passaged continuously for 6 months) revealed a remarkable resemblance to a stage 6-7 post-implantation embryo. The embryonic disc was composed of a polarized, columnar epithelial epiblast (primitive ectoderm) layer separated from a visceral endoderm (primitive endoderm) layer. Electron microscopy of the epiblast revealed apical junctional complexes, apical microvilli, subapical intermediate filaments, and a basement membrane separating the epiblast from underlying visceral endoderm. All of these elements are features of the normal embryonic disc. In the caudal third of the embryonic disc, there was a midline groove, disruption of the basement membrane, and mixing of epiblast cells with underlying endodermal cells (early primitive streak). The amnion was composed of an inner squamous (ectoderm) layer continuous with the epiblast and an outer mesoderm layer. The bilayered yolk sac had occasional endothelial-lined spaces containing possible hematopoietic precursors.

The morphology, immortality, karyotype, and cell surface markers of these marmoset cells identify these marmoset cells as primate ES cells similar to the rhesus ES cells. Since the last cells in the mammalian embryo capable of contributing to both trophectoderm derivatives and endoderm derivatives are the totipotent cells of the early ICM, the ability of marmoset ES cells to contribute to both trophoblast and endoderm demonstrates their similarities to early totipotent embryonic cells of the intact embryo. The formation of embryoid bodies by marmoset ES cells, with remarkable structural similarities to the early post-implantation primate embryo, demonstrates the potential of marmoset ES cells to participate in complex developmental processes requiring the interaction of multiple cell types.

Given the reproductive characteristics of the common marmoset described above (efficient embryo transfer, multiple young, short generation time), marmoset ES cells will be particularly useful for the generation of transgenic primates. Although mice have provided invaluable insights into gene function and regulation, the anatomical and physiological differences between humans and mice limit the usefulness of transgenic mouse models of human diseases. Transgenic primates, in addition to providing insights into the pathogenesis of specific diseases, will provide accurate animal models to test the efficacy and safety of specific treatments.

I claim:

1. A pluripotent primate embryonic stem cell line that (i) proliferates in an in vitro culture for over one year, (ii) maintains the potential to differentiate to derivatives of endoderm, mesoderm, and ectoderm tissues, (iii) is inhibited from differentiation when cultured on a fibroblast feeder layer, (iv) is negative for the SSEA-1 cell surface marker and positive for alkaline phosphatase and the SSEA-3, Tra-1-60, Tra-1-81, and SSEA-4 cell surface markers, and (v) forms teratomas and not teratocarcinomas when injected into an immunocompromised mouse.

2. The cell line of claim 1, wherein the cell line spontaneously differentiates to trophoblast and, wherein said trophoblast produces chorionic gonadotropin when cultured beyond confluence.

3. The cell line of claim 2, wherein the cell line differentiates to trophoblast that produces chorionic gonadotropin when cultured for two weeks beyond confluence.

4. The cell line of claim 1, wherein the cells are and remain euploid for more than one year of continuous culture.

5. The cell line of claim 1, wherein the cells differentiate into cells derived from mesoderm, endoderm and ectoderm germ layers when injected into a SCID mouse.

6. The cell line of claim 1, wherein the cells are human.

* * * * *